United States Patent [19]
Citterio et al.

[11] Patent Number: 5,289,818
[45] Date of Patent: Mar. 1, 1994

[54] SINGLE-DOSE SPRAY-DISPENSER FOR ENDONASAL ADMINISTRATION OF LIQUID MEDICAMENTS

[75] Inventors: Gianfranco Citterio; Maurizio Rusconi, both of Merate, Italy

[73] Assignee: Promo Pack S.A., Italy

[21] Appl. No.: 793,795

[22] Filed: Nov. 18, 1991

[30] Foreign Application Priority Data

Nov. 21, 1990 [IT] Italy ................ 22137 A/90

[51] Int. Cl.⁵ ............................................. A61M 11/00
[52] U.S. Cl. ............................ 128/200.14; 128/200.22
[58] Field of Search ................ 128/200.14, 200.22; 604/210

[56] References Cited

U.S. PATENT DOCUMENTS

| | | | |
|---|---|---|---|
| 3,144,867 | 8/1964 | Trupp et al. | 128/200.22 |
| 3,923,059 | 12/1975 | Ogle | 604/413 |
| 4,946,069 | 8/1990 | Fuchs | 604/210 |
| 5,024,355 | 6/1991 | Jouillat et al. | 222/162 |

FOREIGN PATENT DOCUMENTS

| | | |
|---|---|---|
| 0334349 | 9/1989 | European Pat. Off. . |
| 0378935 | 7/1990 | European Pat. Off. . |
| 0388651 | 9/1990 | European Pat. Off. . |
| 827592 | 4/1938 | France .................. 128/200.22 |
| 6600193 | 7/1966 | Netherlands ........... 128/200.22 |

*Primary Examiner*—Edgar S. Burr
*Assistant Examiner*—Aaron J. Lewis
*Attorney, Agent, or Firm*—Steinberg & Raskin

[57] ABSTRACT

The spray-dispenser device (10) dispenses a dose of liquid medicament contained in a cylindrical vial (18) by the action of a piston (26). The device comprises an operating rod (44) for the piston (26) and a channel (37, 50, 52) for connecting the interior of the vial (18) to a spray nozzle (54). The vial (18) is to be thrown away after dispensing. The vial (18) already contains the piston (26), which seals the vial. The piston (26) is automatically connected to the rod (44) on inserting the vial (18) into the body (11). In the piston there is provided a valve which interrupts the emission channel (37, 50, 52). The valve opens as a result of the operation of the piston (26).

11 Claims, 1 Drawing Sheet

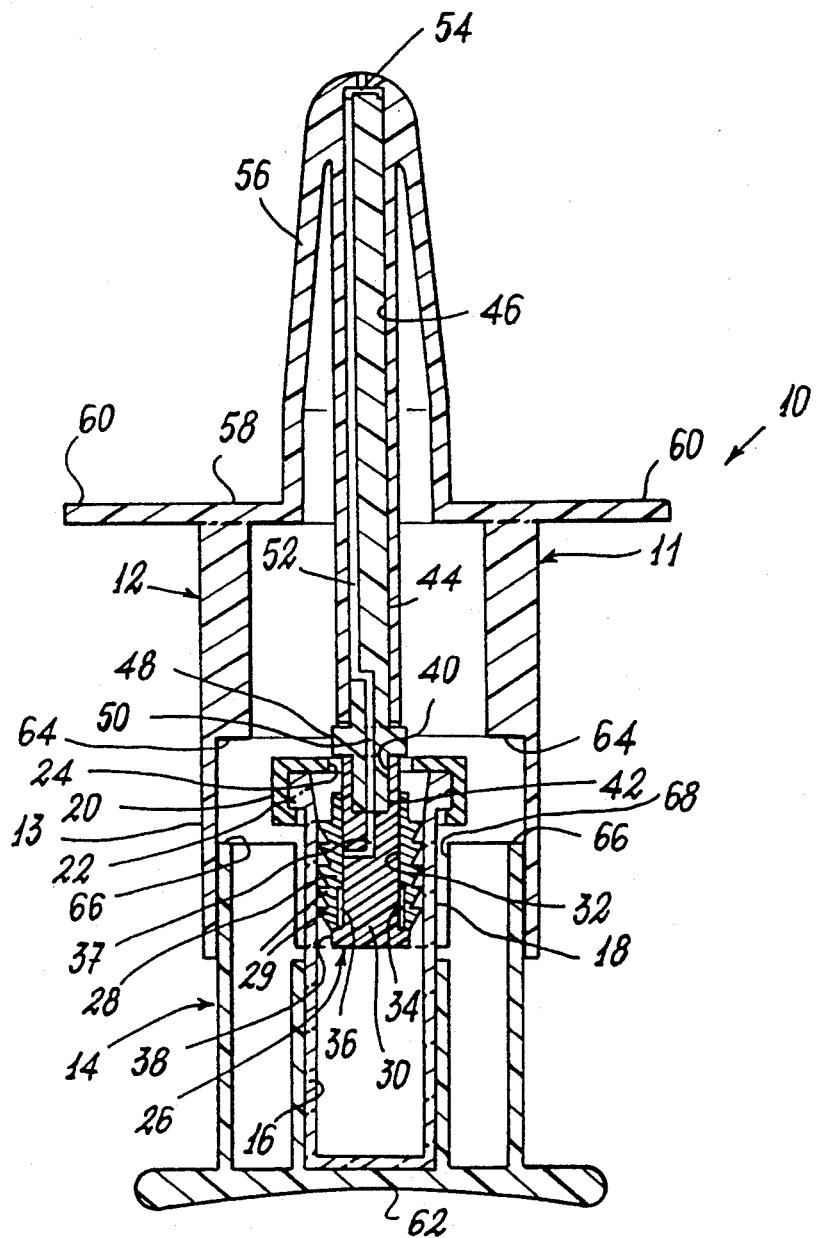

SINGLE-DOSE SPRAY-DISPENSER FOR ENDONASAL ADMINISTRATION OF LIQUID MEDICAMENTS

This invention relates to spray-dispensers for endonasal administration of medicaments in liquid form.

Spray-dispensers of this type are used for administering various pharmacological compounds, including calcitonin.

One known type of spray-dispenser comprises a glass bottle containing a liquid medicament.

The actual dispenser is applied to the container mouth by an internally threaded ring nut screwed onto the threaded neck of the bottle.

The dispenser comprises an overall cylindrical pump arranged vertically coaxial to said ring nut and fixed to this latter. The pump is of the known type which draws a dose of medicament from the container and accumulates it in a suitable chamber when an upwardly projecting vertical stem, with which the pump is provided, is pressed downwards. The medicament is drawn from the bottle through a lower coaxial tube provided on the pump and which dips into the liquid medicament.

The pump operating stem is hollow and its bore connects said accumulation chamber to a spray nozzle. When the stem is again pressed, the dose of medicament contained in the accumulation chamber is expelled outwards through said spray nozzle. This latter forms part of an overall conical adaptor fixed to the stem, and which the patient inserts into a nostril.

Two opposing horizontal fins are also fixed to the adaptor, these enabling the stem to be pressed downwards to hence operate the pump, the stem being maintained in its most upwardly projecting position by a return spring contained in the pump.

The aforesaid briefly described multi-dose spray-dispenser is of rather high cost in that it uses a dispensing pump of high technical characteristics. In addition, as the spray-dispenser is of the type which allows multi-dose administration, it is bulky and heavy.

A further drawback is that after the first delivery, the medicament, and in particular calcitonin, has to be used within a fairly short time otherwise it expires.

A further drawback is that after its initial operating stroke, during which nothing is delivered, the pump delivers only an incomplete dose of medicament for a few more strokes. Hence if the patient uses the device at this time, he inhales an incomplete dose. However, if the patient does not inhale during these initial operating strokes because he is aware of this drawback, a loss of medicament results, this however being taken into account in the quantity fed into the bottle.

A non-reusable single-dose spray-dispenser is also known. It is described in EP-A-0 311 863 and consists of a body into which a cylindrical glass vial containing a single dose of medicament is already inserted. This vial is placed in the spray-dispenser during assembly of its component parts in the factory, and cannot be replaced. When the dose contained in the vial has been dispensed, the entire device including the empty vial is thrown away.

The body of this spray-dispenser contains a piston pump, the piston of which is inserted into the vial and can be pushed down as far as its bottom from an initial position. In a modification of the device, the piston can be moved in two stages to allow one half of a dose to be dispensed at a time. Hence one half of a dose can be fed into one nostril and the other half into the other nostril. The vial and relative piston delimit a pumping chamber which communicates with the spray nozzle.

The piston is integral with a cylindrical rod which can be inserted into a conjugate cavity in said body of the spray-dispenser. The connection between the pumping chamber and the spray nozzle is made by an emission channel, a first part of which is coaxial with the piston. This first part communicates with a second channel part defined by a groove provided in the outer surface of said cylindrical rod and parallel to its axis, and by the relative surface part of the cavity which receives the rod. The cylindrical vial used in such a device is of the type already known prior to the filing of EP-A-0 311 863. The same is true of the dispensing knob, which is of the type used for some time for operating the dispensing valves for pressurized substances contained in cans, or for operating pumps of the foresaid type. The said emission channel has also been known for a long time. Such a channel has for example been used for a considerable time in a TANTUM VERDE ® dispensing device.

However, the spray-dispenser described in EP-A-0 311 863 also has certain drawbacks. Pharmaceutical companies currently specify that a vial of the type used in EP-A-0 311 863 must not be able to be reused. This is not so in the aforesaid case, in which the piston can be easily extracted from the vial by gripping the rod projecting from the vial, this rod being integral with the piston as stated.

Moreover, as stated, when said single-dose spray-dispenser has dispensed the dose contained in the vial it has to be thrown away together with the empty vial, this constituting a considerable wastage.

The object of the present invention is to provide a spray-dispenser for dispensing a dose of liquid medicament contained in a disposable cylindrical vial to be inserted into a suitable seat, the vial not being reusable, even for other uses, whereas the device, apart from the vial, can be reused an indefinite number of times.

Said object is attained by the spray-dispenser device of the present invention, comprising a body for receiving a cylindrical vial containing the dose of liquid medicament, a rod operable from the outside to push the piston to the bottom of the vial in order to deliver through a spray nozzle the medicament dose contained in the vial, the spray nozzle communicating with the interior of the vial via an emission channel interrupted by a valve, characterised in that the piston is already contained as an independent piece within the vial, which when empty can be replaced by another full vial; the connection between the rod and piston being made automatically following the insertion of the vial into said body; said valve being provided within the piston and being opened as a result of operating the rod.

According to a preferred embodiment of the present invention, the piston is formed of an outer annular part which sealedly receives an inner cylindrical part, the two parts being movable relative to each other between a position in which the valve is closed and a position in which it is open following the operation of the rod. According to a further embodiment of the present invention, to increase the degree of protection against reuse of the vial, even for other uses, the vial can be provided with a ring cap, in said ring cap there being provided a coaxial circular hole of diameter substantially less than the inner diameter of the vial, but which allows said rod to pass through it.

This ring cap constitutes a further impediment to the extraction of the piston, and making reuse totally impracticable. Preferably, the dispensing device of the present invention is provided with an emission channel which coaxially traverses the piston and proceeds for a short distance within the lower part of the rod, to open into a groove provided in the lateral surface of this latter, said groove, together with the corresponding part of the surface of the conjugate cavity into which the rod is inserted, defining the remaining channel portion, which communicates with the spray nozzle.

The device is provided with suitable operating fins for pushing the rod inwards in order to operate the piston contained in the vial, in this manner said piston being pushed to the bottom thereof. The consequent opening of the valve provided within the piston connects the vial interior to the spray nozzle, from which the dose of medicament emerges in the form of a spray.

As can be imagined, once the piston has reached the bottom of the capsule, it is impossible in practice to extract it, especially if said ring cap has also been provided. In this respect, to extract the piston, the ring cap has firstly to be removed, this being difficult in practice even if suitable tools are available. Having done this, the piston must be withdrawn from the bottom of the vial, this being impossible without suitable tools.

However, even in the absence of the ring cap there is considerable safety against reuse of the vial, especially if the seal lips between the vial and piston are of sawtoothed shape with unequal sides, this in practice preventing extraction of the piston while allowing the piston to be pushed to the bottom of the vial. It should also be noted that even if suitable tools are available, the grip exerted by said tools on the upper part of the piston would in any case ruin its traversing channel and the relative valve, making it practically impossible to reuse another vial of conventional type, i.e. without an already inserted piston.

Apart from the vial and the relative piston contained therein, the device of the present invention can be reused an indeterminate number of times. In this respect, to dispense a new dose it is sufficient merely to remove the empty vial and replace it with a new one.

According to a further modification of the invention the spray-dispenser can be provided with means for dispensing the dose of medicament contained in the vial in two partial doses. These means can consist of stops inserted into the path of operation of the device, so that the operating stroke can be continued only by rotating one part of the body of the device relative to the other.

The invention will be more apparent from the description of one embodiment thereof given hereinafter by way of non-limiting example. In this description reference is made to the accompanying drawing, the single FIGURE of which represents a vertical longitudinal section through the spray-dispenser of the invention.

From the FIGURE it can be seen that the spray-dispenser 10 comprises a casing consisting of an upper body 12 and a lower body 14 insertable into the lower aperture of the upper body. The lower part 13 of the upper body 12 is of circular cross-section. The cross-section of the lower body is also circular and is of such dimensions that it can be inserted from below into the lower part 13 of the upper body 12.

In its interior, the lower body 14 comprises a coaxial cylindrical seat 16 into which a vial 18 can be inserted. This latter is closed at its top by a ring cap 20 which embraces the lip 22 of the mouth of the vial 18. The ring cap 20 has a circular hole 24 of diameter substantially less than the inner diameter of the vial 18.

A tight fitting piston 26 of suitable plastics material is provided in the upper part of the interior of the vial 18. The piston 26 consists of an outer annular part 28 provided with seal lips of sawtoothed cross-section, which seal against the inner wall of the vial 18, and an inner cylindrical part 30 slidable axially in a sealed manner within the inner cylindrical cavity 32 of the outer annular part 28 of the piston 26. The lower portion 34 of the cylindrical cavity 32 is of greater diameter, to create an annular interspace or chamber 36. In the inner cylindrical part 30 of the piston 26 there is provided an L-shaped channel 37, the vertical side of the L being coaxial to the piston 26, whereas the horizontal side of the channel 37 extends radially and opens into the interface surface between the outer annular part 28 and the inner cylindrical part 30 of the piston 26. The inner cylindrical part 30 has a lower greater-diameter portion 38 forming a step and which, when the piston 26 is in that position which it occupies when the vial 18 is sold (which is as shown in the figure), acts as a seal against the lower edge of the outer annular part 28 of the piston 26.

In the vial 18 as sold, the upper end of the inner cylindrical part 30 of the piston 26 is at the same level as the upper surface of the ring cap 20 and hence does not project from this latter. Between the free surface (not shown in the figure) of the liquid medicament contained in the vial 18 and the piston 26 there is a certain space which enables the inner cylindrical part 30 of the piston to descend through a certain distance relative to the outer annular part 28.

In the upper end of the inner cylindrical part 20 of the piston 26 there is a coaxial blind hole or cylindrical cavity 40. When the vial 18 is inserted into its seat 16 in the lower body 14 of the spray-dispenser 10, achieved by withdrawing the lower body 14 from the upper body 12, and the lower body 14 is again inserted into the upper body 12, the lower end 42 of a rod 44 is automatically inserted as a lightly forced fit into the cavity 40 of the piston 26, to hence form a male-female connection between the piston 26 and rod 44. This rod is of overall elongate cylindrical shape with most of its length inserted into a conjugate cavity 46 forming part of the upper body 12 of the spray-dispenser 10. In addition to the lower end 42 of the rod 44, there emerges from the cavity 46 only an adjacent collar-shaped portion 48, which seals against the upper end of the inner cylindrical part 30 of the piston 26. Through a short portion of its lower part the rod 44 comprises a channel portion 50 of inverted L shape, the vertical branch of which represents the extension of the corresponding vertical portion of the channel 37 in the piston 26. The horizontal portion of the channel 50 opens into a vertical groove 52 provided in the outer cylindrical surface of the rod 44 which, together with the relative surface part of the cavity 46 into which the rod 44 is inserted, forms a further channel portion 52 which terminates upperly in the spray nozzle 54.

The upper body 12 of the spray-dispenser 10 comprises a nasal adaptor 56 insertable into a nostril and extending upwards from a horizontal ledge 58 of which two outwardly projecting opposing fins 60 also form part, to act as a grip for operating the device 10.

The spray-dispenser 10 is used in the following very simple manner.

Having separated the two bodies 12 and 14 of the device 10 and inserted the relative vial 18 containing a dose of medicament into its seat 16 in the lower body 14, the lower body 14 is inserted into the upper body 12, so that the device 10 is in the configuration illustrated in the figure, i.e. with the lower end 42 of the rod 44 automatically inserted into its cavity 40 in the piston 26. The device 10 is then ready for operation after the user has inserted the adaptor 56 into a nostril. It is then necessary only to press the fins 60 of the upper body 12 downwards and the base 62 of the lower body 14 simultaneously upwards with the fingers to cause the two bodies 12 and 14 to approach each other. As a result the rod 44 pushes the inner cylindrical part 30 of the piston 26 downwards relative to its outer annular part 28, until the lower edge of the collar 48, which enters the vial 18 through the aperture 24 in the ring cap 20, rests against the upper edge of the outer annular part 28 of the piston 26. As a result, the piston valve is opened to connect the interior of the vial 18 to the spray nozzle 54. In this respect, the L-shaped channel 37 is now in communication with the annular chamber 36 which itself communicates lowerly with the interior of the vial 18 in that the lower projecting portion 38 of the inner cylindrical part of the piston 26, being lowered, no longer seals against the lower edge of the outer annular part 28 thereof.

Continuing to press on the fins 60 and base 62, the rod 44 pushes the piston 26 to the bottom of the vial 18, to cause the complete delivery of the dose of liquid medicament contained in the vial 18 through the spray nozzle 54.

The spray-dispenser shown in the figure is provided with means to enable one half of a dose of medicament to be delivered at a time. This enables the patient to inhale one half of the dose through one nostril and the other half through the other nostril.

To obtain this result, the upper body 12 of the device 10 comprises two shoulders 64 of limited width in the direction perpendicular to the plane of the figure, and against which the upper end 66 of the lower body 14 abuts when the piston 26, during its downward stroke, has already expelled from the vial 18, and hence from the spray nozzle 54, one half of the dose of medicament contained in the vial.

The cylindrical part of the lower body 14 comprises two notches 68 (of which only one is visible in the figure) arranged at 90° to the shoulders 64. On rotating the lower body 14 through 90° about the upper body 12 of the device 10, so that the notches 68 coincide with the shoulders 64, the pressing action can be continued to move the piston 26 to the bottom of the vial 18, hence delivering the other half dose of medicament contained in the vial.

As can be seen, the described inhaler is extremely simple and hence of low cost. In addition, apart from the vial with its piston, to be thrown away after use, the device can be reused an indefinite number of time. It is particularly suitable for administering calcitonin and similar medicaments.

We claim:

1. A spray dispenser device (10) for dispensing a dose of liquid medicament contained in a cylindrical vial by the action of a piston to be pushed to the bottom of said vial, said device comprising a body (11) for receiving a cylindrical vial (18) containing the dose of liquid medicament, a piston (26), a rod (44) operable from the outside to push said piston (26) to the bottom of the vial (18) and to thereby form an emission channel (37, 50, 52) between a spray nozzle (54) and the interior of the vial (18) in order to deliver the medicament dose contained in the vial through the spray nozzle, said piston (26) being separated from said rod and contained as an independent piece with the vial (18), which when empty can be replaced by another full vial; a connection between the rod (44) and piston (26) being made automatically following the insertion of the vial (18) into said body (11), said piston (26) having an outer annular part (28) which sealedly receives an inner cylindrical part (30), the two parts (28, 30) being movable relative to each other between a position in which the emission channel (37, 50, 52) is closed and a position in which it is open following the operation of the rod (44).

2. A device (10) as claimed in claim 1, wherein the vial (18) is also provided with a ring cap (20), in which there is provided a coaxial circular hole (24) of diameter substantially less than the inner diameter of the vial, but which allows said rod (44) to pass through it.

3. A device (10) as claimed in claim 1, wherein the emission channel (37, 50, 52) connecting the interior of the vial (18) to the spray nozzle (54) comprises a short portion coaxial to the rod (44) at that end of the rod adjacent to the vial, said portion communicating with the piston (26) and with a groove, parallel to the axis of the rod (44) provided in its lateral surface, said groove, together with the relative part of the surface of the cavity (46) into which the rod (44) is inserted, defining that part of said channel which opens into the spray nozzle (54).

4. A device (10) as claimed in claim 1, provided with means (64, 68) for dispensing the dose of medicament contained in the vial (18) in two stages, a half dose at a time.

5. A device as claimed in claim 1, wherein said body comprises an upper portion and a lower portion insertable into an aperture of said upper portion.

6. A device as claimed in claim 5, wherein said lower portion comprises a coaxial cylindrical seat into which said vial is inserted.

7. A device as claimed in claim 1, wherein said outer annular part is provided with seal lips of saw-toothed cross-sectional shape which seal against an inner wall of said vial.

8. A device as claimed in claim 1, wherein said inner cylindrical part is arranged slidably and axially in a sealed manner with an inner cylindrical cavity arranged on said outer annular part.

9. The device as claimed in claim 8, wherein said cylindrical cavity has a lower portion having a greater diameter such that an annular interspace is defined between said inner cylindrical part and said cylindrical cavity.

10. The device as claimed in claim 1, wherein said inner cylindrical part comprises an L-shaped channel, a vertical side of said channel being arranged coaxial to said piston, a horizontal side of said channel extending radially and opening into an interface surface between said outer annular part and said inner cylindrical part.

11. A spray dispenser device for dispensing a dose of liquid medicament contained in a cylindrical vial by the action of a piston to be pushed to the bottom of said vial, said device comprising a body for receiving a cylindrical vial containing the dose of liquid medicament; a piston; a rod operable from the outside to push said piston to the bottom of the vial and to thereby form an emission channel between a spray nozzle and the interior of the vial in order to deliver the medicament dose contained in the vial through the spray nozzle, said piston being separate from said rod and contained as an independent piece with the vial, which when empty can be replaced by another full vial; a connection between the rod and piston being made automatically following the insertion of the vial into said body, said vial being provided with a ring cap, in which there is provided a coaxial circular hole of diameter substantially less than the inner diameter of the vial, but which allows said rod to pass through it.

* * * * *